United States Patent [19]

Ueda et al.

[11] Patent Number: 5,578,472
[45] Date of Patent: Nov. 26, 1996

[54] PROCESS FOR THE PRODUCTION OF ETHANOL FROM MICROALGAE

[75] Inventors: Ryohei Ueda; Shin Hirayama; Kiyoshi Sugata; Hiroshi Nakayama, all of Yokohama, Japan

[73] Assignee: Mitsubishi Jukogyo Kabushiki Kaisha, Tokyo, Japan

[21] Appl. No.: 310,769

[22] Filed: Sep. 27, 1994

[30] Foreign Application Priority Data

Sep. 27, 1993 [JP] Japan ................................. 5-239845
Sep. 27, 1993 [JP] Japan ................................. 5-239846

[51] Int. Cl.$^6$ ...................... C12P 7/14; C12P 7/08; C12P 7/12; C12N 1/12
[52] U.S. Cl. ............. 435/161; 435/162; 435/163; 435/165; 435/166; 435/42; 435/946
[58] Field of Search ................. 435/161, 163, 435/946, 162, 166, 41, 42, 291, 313, 316

[56] References Cited

U.S. PATENT DOCUMENTS

| | | | |
|---|---|---|---|
| 4,288,550 | 9/1981 | Ishida et al. | 435/161 |
| 4,358,537 | 11/1982 | Chynoneth | 435/161 |
| 5,270,175 | 12/1993 | Moll | 435/41 |

FOREIGN PATENT DOCUMENTS 1493480  12/1975  United Kingdom.

OTHER PUBLICATIONS

Miura et al. *Appl Biochem Biotechnol*(39–40) 1993. 753–61.
Ohta et al. *Plant Physiol.* 83(4). 1987. pp. 1022–1026.

Primary Examiner—Chhaya D. Sayala
Assistant Examiner—Blaine Lankford
Attorney, Agent, or Firm—Jacobson, Price, Holman & Stern, PLLC

[57] ABSTRACT

The present invention provides a process and system for the production of ethanol wherein a microalga capable of accumulating starch in the cells thereof is cultured, the culture solution containing the grown algal cells is concentrated, and ethanol is formed by maintaining the resulting slurry in a dark and anaerobic atmosphere while keeping its pH in the range of 6.0 to 9.0. This process and system can further include additional steps and units for subjecting the residual slurry, from which ethanol has been separated, to methane fermentation, burning it to generate carbon dioxide, and using the carbon dioxide in the microalga culturing step.

4 Claims, 3 Drawing Sheets

PROCESS FOR THE PRODUCTION OF ETHANOL FROM MICROALGAE

FIELD OF THE INVENTION AND RELATED ART STATEMENT

This invention relates to a process for the production of ethanol useful as fuel, raw material for chemical industry, and the like, by using starch accumulated in microalgae as the starting material, as well as a system for carrying out the process.

Conventionally, ethanol is produced by a chemical synthesis process in which ethanol is synthesized from fossil resources (e.g., coal and petroleum) via ethylene, or by a fermentation process in which ethanol is produced from biomass resources (e.g., cane sugar and corn starch) with the aid of microorganisms such as molds and yeast.

As to biomass materials, some of the microalgae which are minute photosynthetic organisms typified by *Chlorella, Dunaliella, Chlamydomonas, Scenedesmus, Spirulina* and the like are known to contain a large amount (more than 50% of the dry weight) of starch and glycogen useful as raw materials for the production of ethanol, and some processes for the production of ethanol by using such microalgal starch as the starting material have been proposed.

Conventionally, the production of ethanol by using such microalgal starch as the starting material has been carried out according to the following procedure:

In a first step, a microalga is grown by culturing it photoautotrophically in the presence of light through carbon dioxide assimilation by photosynthesis, or by culturing it heterotrophically in the dark and in the presence of organic materials such as sugars and organic acids.

In a second step, since the grown microalga stores starch mainly in the cells thereof, the starch is released from the cells with the aid of a mechanical means (e.g., ultrasonic or explosive disintegration) or an enzyme for the dissolution of cell walls. Then, the starch is separated by extraction with water or an organic solvent.

In a third step, the starch separated by extraction is hydrolyzed to glucose with the aid of saccharogenic amylase or the like. This glucose is fermented by the addition of alcohol yeast and thus converted into ethanol.

SUMMARY OF THE INVENTION

The above-described conventional processes involve the following problems:

First, it is necessary to separate intracellular starch by extraction. However, since many microalgae have strong cell walls, much power is consumed for purposes of mechanical cell disintegration, or an expensive enzyme for the dissolution of cell walls is required. Moreover, a large amount of organic solvent and much power for centrifugation are required in the starch extraction step.

Secondly, since the starch separated by extraction is raw, the starch must be subjected to a heat treatment step (called "gelatinization" or "conversion into a-starch") before it is hydrolyzed to glucose with the aid of saccharogenic amylase or the like. The large amount of heat energy required for this purpose presents a problem. Usually, this heat energy is believed to comprise 20 to 30% of the total energy consumed in the ethanol production process.

Owing to these problems, microalgal starch has not yet been put to practical use on a large scale for all its many advantages over agricultural products such as potatoes and corn.

It is a first object of the present invention to provide a process for the production of ethanol from starch-accumulating microalgae which can solve the above-described problems of the prior art by making it possible to produce ethanol simply and efficiently without requiring large amounts of energy and chemicals, as well as a system for carrying out this process.

In order to accomplish the above object, the present inventors made an investigation on the means for facilitating the extractive separation of starch from microalgal cells and for reducing the high energy cost required to heat the raw starch. In the course of this investigation, it has been found that, by effectively utilizing the alcoholization reaction of intracellular starch which is peculiar to microalgae, ethanol can be produced without using the extractive separation of starch from cells and its heat treatment.

Thus, according to a first aspect of the present invention, there are provided:

a process for the production of ethanol from microalgae which comprises the steps of culturing a microalga capable of accumulating starch in the cells thereof; concentrating the culture solution containing the grown algal cells; and maintaining the resulting slurry in a dark and anaerobic atmosphere to form ethanol, while keeping its pH in the range of 6.0 to 9.0; and a system for the production of ethanol from microalgae which comprises culture means for culturing a microalga capable of accumulating starch in the cells thereof; concentration means for concentrating the culture solution; maintenance means for maintaining the concentrated algal cell slurry in a dark and anaerobic atmosphere; pH regulation means for regulating the pH within the maintenance means; and separation and concentration means for separating and concentrating the ethanol so formed.

Microalgae can carry out photosynthesis under illumination with sunlight or the like and thereby accumulate starch in the cells thereof. Moreover, some microalgae can also grow under dark conditions in the presence of organic nutrients such as sugars and thereby accumulate starch.

On the other hand, in the absence of light and organic nutrients, microalgae usually maintain their life by consuming the materials (such as starch) stored in the cells and decomposing them oxidatively to carbon dioxide. Under these conditions, the production of ethanol does not take place. However, it has been found that, if dark and oxygen-free anaerobic conditions are artificially established, the oxidative reaction of starch to carbon dioxide does not proceed to completion. Thus, depending on the type of the microalga, hydrogen gas, carbon dioxide, ethanol, lactic acid, formic acid, acetic acid and the like are produced in varying proportions.

The present inventors examined various starch-accumulating microalgae for the productivity of ethanol from intracellular starch, by culturing the microalgae, concentrating the culture solutions, and maintaining the resulting algal cell slurries in a dark and anaerobic atmosphere. As a result, it has been found that some microalgae have especially high ethanol productivity and the use of such microalgae enables efficient production of ethanol.

The microalgae which can be used as starting materials for the production of ethanol in the process of the present invention are ones characterized by containing a large amount (preferably more than 50% of the dry weight) of polysaccharides composed of glucose, such as starch, glycogen and the like, in the cells and also by metabolizing such starch, glycogen and the like rapidly in a dark and anaerobic atmosphere to form a large amount of ethanol. Examples of the microalgae meeting these requirements include ones classified into the classes Chlorophyceae, Prasinophyceae, Cryptophyceae and Cyanophyceae. More specifically, typical genera belonging to the class Chlorophyceae include *Chlamydomonas* and *Chlorella,* and typical genera belonging to the class Cyanophyceae include *Spirulina, Oscillatoria* and *Microcystis.*

When a slurry containing such a microalga is maintained in a dark and anaerobic atmosphere to form ethanol, organic acids, though in slight amounts, are formed in addition to ethanol. Consequently, the pH of the culture solution is gradually reduced as the reaction proceeds. Since the reaction for the formation of ethanol slows down at pH values lower than a certain level, the pH of the microalga-containing slurry should be regulated so as to remain in the range of 6.0 to 9.0, preferably 6.5 to 8.0, during the period in which the slurry is maintained in a dark and anaerobic atmosphere according to the process of the present invention.

If the pH is less than 6.0, the rate of formation of ethanol will become unduly slow. On the other hand, if the pH is greater than 9.0 as a result of the oversupply of alkali for pH regulation, the rate of formation of ethanol will become unduly slow again.

One embodiment of the process for the production of ethanol in accordance with the present invention is illustrated in FIG. 1.

In the process of FIG. 1, any of the above-described microalgae capable of accumulating starch in the cells thereof is supplied to and cultured in microalga culturing means 1. In the case of photoautotrophism as described above, the microalga culturing means 1 can be a culture vessel of the water channel type having an open top and a water depth of about 10 to 30 cm, in which the microalga is cultured by exposure to sunlight in the presence of inorganic nutrients such as nitrogen- and phosphorus-containing minerals.

In the case of heterotrophism, exposure to light is unnecessary. Using a conventionally known common fermenter and an organic nutrient medium, a microalga may be cultured after the fermenter and the culture medium have been sterilized at 120° C. for about 15 minutes.

When the density of the microalga in the culture solution has reached a level of about 0.1 to 1.0 g per liter of the culture solution, the cultivation is discontinued. Then, the culture solution is concentrated in microalga concentration means 2.

If the microalga is highly precipitable, the culture solution is first concentrated by natural precipitation in the microalga concentration means 2 so as to have a solid content of about 1%, and further concentrated by centrifugation, a belt filter or the like so as to have a solid content of 10 to 20%. If the microalga is less precipitable, the culture solution is directly concentrated by centrifugation, a belt filter or the like so as to have a solid content of 10 to 20%.

In this process, the culture solution should be concentrated to as high a solid content as possible (i.e., 10 to 20%), provided that its flowability is retained. This makes it possible to handle the resulting slurry easily, agitate it gently in a subsequent step, and raise the ethanol concentration to such an extent as to be advantageous to a later ethanol concentration step.

The microalga-containing slurry thus obtained is introduced into maintenance means 3 where it is maintained in a dark and anaerobic atmosphere to form ethanol. The maintenance means 3 comprises a closed vessel equipped with a pH monitor and a gentle agitation means such as slurry pump or stirrer. As used herein, the term "dark atmosphere" means that light is intercepted to such an extent as to prevent photosynthesis.

The microalga-containing slurry is introduced into this maintenance means 3 and maintained in a dark and anaerobic atmosphere with gentle agitation to form ethanol. During this period, the pH of the slurry is monitored with the pH monitor and kept in the range of 6.0 to 9.0, preferably 6.5 to 8.0, by adding an alkaline solution (e.g., of NaOH) or an acid solution (e.g., of HCl) to the slurry with the aid of pH regulation means 4 equipped with a device for the supply of alkaline and acid solutions. The pH regulation means 4 may be adapted to operate in conjunction with the pH monitor of the maintenance means 3 so that the pH of the slurry can be regulated continuously.

The residence time of the microalga in the maintenance means 3 may vary according to the type of the microalga, the maintenance conditions employed, and the like. However, it generally ranges from 5 to 50 hours.

When the ethanol concentration in the slurry has reached a level of about 5 to 50 g per liter (i.e., 5,000 to 50,000 ppm), the slurry is transferred to ethanol separation and concentration means 5 where ethanol is separated and concentrated.

In the ethanol separation and concentration means, there may be employed any of various techniques including distillation, concentration with an ethanol or water separating membrane, and supercritical extraction with a solvent such as propane. Thus, the ethanol can be concentrated to any desired concentration ranging up to that of absolute ethanol.

The residue obtained after the separation of ethanol can be dried and disposed of by incineration or the like.

According to the present invention, ethanol can be produced simply by culturing a microalga capable of accumulating starch, harvesting and concentrating the grown algal cells, and maintaining the concentrated algal cell slurry in a dark and anaerobic atmosphere with gentle agitation while keeping its pH in the range of 6.0 to 9.0.

All of these operations involve a slight cost and a slight amount of energy, so that the cost and energy required in the conventional process for disintegration of the concentrated microalgal cells, extractive separation of starch, and heat treatment of starch can be greatly reduced (to one-tenth or less). Moreover, ethanol can produced according to a much simplified procedure.

The above-described process utilizing the alcoholization reaction of intracellular starch which is peculiar to microalgae still involves the following problems.

First, the fluid from which ethanol has been separated by the ethanol separation and concentration means 5 contains relatively large amounts of microalgal cell components (consisting essentially of proteins and lipids because starch has been substantially depleted), as well as small amounts of residual ethanol, organic acids and the like. If the fluid having such a heavy organic pollution burden is directly discharged from the process, environmental pollution will result in its surroundings.

Secondly, when a microalga is cultured photoautotrophically (e.g., in the presence of sunlight and carbon dioxide) in the microalga culturing means 1, its growth rate is low if atmospheric carbon dioxide alone is used. Consequently, it is necessary to convey and supply a large amount of carbon dioxide from the outside of the system. The cost and energy required for this purpose are not a little.

It is a second object of the present invention to provide a process and system for the production of ethanol from microalgae which can solve the above-described problems by decreasing the organic waste and reducing the amount of carbon dioxide supplied from the outside of the system.

According to a second aspect of the present invention, there are provided:

a process for the production of ethanol from microalgae wherein a starch-containing microalga is cultured, harvested, concentrated and then maintained in a dark and anaerobic atmosphere to form ethanol, the process comprising the steps of:
(a) culturing a microalga capable of accumulating starch in the cells thereof;
(b) concentrating the culture solution containing the grown algal cells to obtain a concentrated algal cell slurry;
(c) maintaining the concentrated algal cell slurry in a dark and anaerobic atmosphere to form ethanol, while keeping its pH in the range of 6.0 to 9.0;
(d) separating and concentrating the ethanol so formed;
(e) subjecting the microalga-containing slurry, from which ethanol has been separated and concentrated, to methane fermentation;
(f) burning the methane-containing fermentation gas generated by the methane fermentation;
(g) drying and burning the residue resulting from the methane fermentation; and
(h) recycling the carbon dioxide generated in steps (c), (f) and (g) to the microalga culturing step; and a system for the production of ethanol from microalgae which comprises culture means for culturing a microalga capable of accumulating starch in the cells thereof; concentration means for concentrating the culture solution; maintenance means for maintaining the concentrated algal cell slurry in a dark and anaerobic atmosphere; pH regulation means for regulating the pH within the maintenance means; separation and concentration means for separating and concentrating the ethanol so formed; methane fermentation means for subjecting the microalga-containing slurry, from which ethanol has been separated and concentrated, to methane fermentation; first combustion means for burning the methane-containing fermentation gas generated by the methane fermentation; second combustion means for drying and burning the residue resulting from the methane fermentation; and carbon dioxide recycling means for recycling the carbon dioxide generated in the maintenance means, the first combustion means and the second combustion means to the microalga culturing step.

Thus, the second aspect of the present invention is characterized by the fact that, in a process for the production of ethanol wherein a starch-containing microalga is cultured, harvested, concentrated and maintained in a dark and anaerobic atmosphere to form ethanol, the residual slurry from which ethanol has been separated is subjected to methane fermentation, the methane so generated and the residue resulting from the methane fermentation are burned to recover energy and generate carbon dioxide, and this carbon dioxide is used in the microalga culturing step together with the carbon dioxide generated as a by-product in the ethanol formation step.

FIG. 4 is a flow diagram illustrating the ethanol production process in accordance with the second aspect of the present invention. The means 1–5 illustrated in FIG. 4 are the same as those of the process illustrated in FIG. 1. The microalga-containing slurry, from which ethanol has been separated and concentrated, is withdrawn from the ethanol separation and concentration means 5 and introduced into methane fermentation means 6 where it is kept at about 35° C. with gentle agitation while being isolated from atmospheric oxygen. Thus, under the action of coexisting anaerobic microorganisms, the organic components present in the slurry are decomposed to low-molecular compounds and finally converted to methane and carbon dioxide.

It has hitherto been unknown to what extent starch-containing microalgae can be subjected to methane fermentation after they are maintained in a dark and anaerobic atmosphere to form ethanol. As a result of experiments conducted by the present inventors, it has been found that 60 to 70% of the introduced organic matter is decomposed. It has also be found that methane is generated in a volume of 0.2 to 0.3 $Nm^3$ per kilogram of the introduced organic matter and, at the same time, carbon dioxide is generated in a volume equal to about 80 to 100% of the volume of methane.

The methane and carbon dioxide so generated are received into gaseous mixture collection means 7 comprising, for example, a floating roof type gas holder or the like. Since the gaseous mixture of methane and carbon dioxide has a high calorific value (about 5,000 $kcal/Nm^3$), it may be utilized as fuel. That is, the gaseous mixture may be burned in combustion means 8, and the heat so produced may be recovered by means of a boiler and used for purposes of electric power generation or the like. Moreover, the fermentation residue withdrawn from the methane fermentation means 6 is introduced into fermentation residue drying means 9 where it is centrifuged as required and the resulting solid matter is dried in the sun. Then, the dried residue may be burned in the combustion means 8 to recover heat.

Thus, by subjecting the residual slurry withdrawn from the ethanol separation and concentration means 5 to methane fermentation and then drying and burning the residue resulting from the methane fermentation, the organic matter present in the residual slurry can be decreased to a level of about 1/10 to 1/30. Consequently, the amount of organic waste discharged from the ethanol production process can be greatly reduced.

The amount of organic waste can further be reduced to a nearly zero level solely by the addition of a simple after-treatment step such as treatment with activated sludge.

In the combustion gas exhausted from the combustion means 8, the greater part of the carbon present in the residual slurry withdrawn from the ethanol separation and concentration means 5 is recovered and contained in the form of carbon dioxide. This carbon dioxide can be utilized as an inorganic carbon source necessary for the cultivation of the microalga by supplying it to the microalga culturing means 1.

Moreover, when the microalga is maintained in a dark and anaerobic atmosphere within the maintenance means 3, its intracellular starch is decomposed and converted into ethanol. During this process, about one-half of the decomposed starch is discharged into a gaseous phase as carbon dioxide. If this carbon dioxide is collected by generated gas collection means 10 such as a floating roof type gas holder or the like and suitably supplied to the microalga culturing means 1, it can be utilized as an inorganic carbon source for the cultivation of the microalga.

That is, a considerable portion of the carbon dioxide required in the microalga culturing means 1 can be supplied by utilizing the carbon dioxide obtained from the combustion means 8 and the generated gas collection means 10. Thus, the carbon dioxide conveyed and supplied from the outside can be greatly decreased.

According to the present invention, the residual slurry resulting from the formation of ethanol by a microalga is subjected to methane fermentation and the residue resulting from the methane fermentation is removed as solid matter, so that the amount of organic waste discharged from the ethanol production process to the outside of the system can be greatly reduced (to a level of 1/10 to 1/30). Thus, a good environment can be maintained in its surroundings.

Moreover, both the carbon dioxide obtained by burning the methane fermentation gas and the dried fermentation residue, together with the carbon dioxide generated in the maintenance means for maintaining the microalga-containing slurry in a dark and anaerobic atmosphere, is recycled to the microalga culturing means, so that 60 to 70% of the carbon dioxide necessary for the cultivation of the microalga can be supplied. Thus, the cost of carbon dioxide conveyed and supplied from the outside of the system can be greatly reduced.

DETAILED DESCRIPTION OF PREFERRED EMBODIMENTS

The process and system in accordance with the first aspect of the present invention are more specifically explained with reference to the following examples.

Example 1 (Effect of pH on ethanol formation)

*Chlamydomonas reinhardtii* UTEX2247 was cultured in a culture solution composed of culture media A to E having the respective compositions shown in Table 1. More specifically, this culture solution was prepared by mixing 1 ml of A, 10 ml of B, 10 µl of C, 100 ml of D and 6 ml of E, adding water to make a total volume of 1 liter, and adjusting the solution to pH 8.0 with NaOH.

Two liters of this culture solution and 0.04 g of a stock culture of the above-described *Chlamydomonas* strain were placed in a flat, transparent vessel and cultured at 25° C. for 3 days under continuous illumination at about 15,000 lux with a white fluorescent lamp and with the passage of air (having 5% $CO_2$ added thereto). Thus, there was obtained a culture solution containing 1.5 g (dry weight) of algal cells in the volume of 2 liters.

Then, this culture solution was concentrated by centrifugation to obtain an algal cell slurry containing 1.5 g of cells of *Chlamydomonas reinhardtii* UTEX2247 in a volume of 16 ml. This slurry was divided into 8 samples each comprising 2 ml of the slurry. Twenty milliliters each of 8 universal buffers (i.e., Britton-Robinson buffers comprising $H_3PO_4$, acetic acid, boric acid and NaOH) having different pH values ranging from 4 to 11 were separately added to and mixed with the above samples, followed by centrifugation. This procedure was repeated twice to obtain a total of 8 algal cell slurries (containing 0.19 g of algal cells in the volume of 2 ml) adjusted to different pH values ranging from 4 to 11. Two milliliters each of these algal cell slurries were transferred to 10-ml vessels. After nitrogen gas was injected into the slurries for a short period of time to expel oxygen from the vessels, they were tightly covered and shaken (at a rate of 65 strokes per minute) at 25° C. under dark conditions to form ethanol. After 48 hours of shaking, the concentration of ethanol formed in each slurry was determined. The results thus obtained are shown in FIG. 2.

Figure 2:
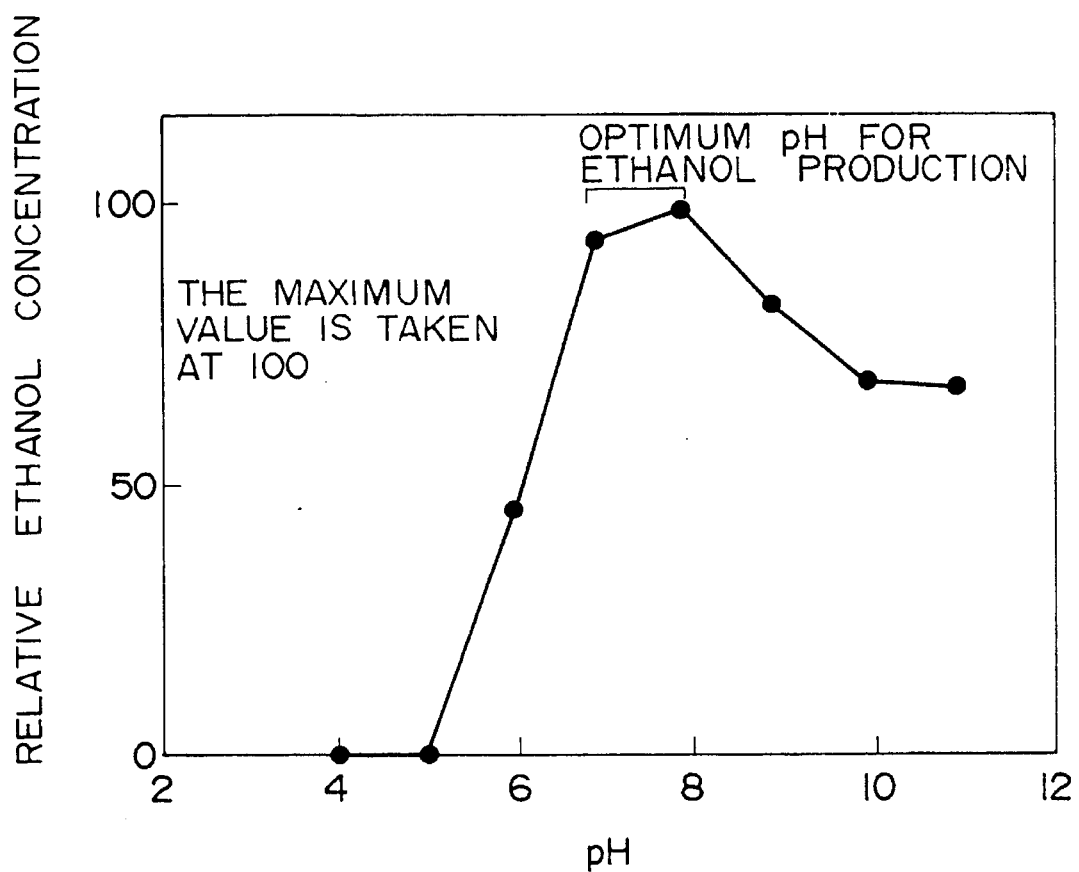
FIG. 2 is a graph showing the effect of pH on the formation of ethanol by a microalga maintained in a dark and anaerobic atmosphere.

It can be seen from the results of FIG. 2 that the pH at which ethanol is produced from microalgae according to the process of the present invention is preferably in the range of 6 to 9 and more preferably in the range of 6.5 to 8.0.

Example 2 (Production of alcohol from a green alga of the genus *Chlamydomonas*)

*Chlamydomonas reinhardtii* UTEX2247 was cultured in a culture solution composed of culture media A to E having the respective compositions shown in Table 1. More specifically, this culture solution was prepared by mixing 1 ml of A, 10 ml of B, 10 µl of C, 100 ml of D and 6 ml of E, adding water to make a total volume of 1 liter, and adjusting the solution to pH 8.0 with NaOH.

Fifty liters of this culture solution and a stock culture of the above-described *Chlamydomonas* strain (in an amount equivalent to 1.0 g of dried algal cells) were placed in a flat, transparent vessel and cultured at 25° C. for 3 days under continuous illumination at about 15,000 lux with a white fluorescent lamp and with the passage of air (having 5% $CO_2$ added thereto). Thus, there was obtained a culture solution containing 38 g (dry weight) of algal cells in the volume of 50 liters.

TABLE 1

| Culture media for *Chlamydomonas reinhardtii* UTEX2247 | | |
|---|---|---|
| Designation | Composition of culture medium | |
| A | $MgSO_4.7H_2O$ | 4.0 g |
| | Sodium glycerophosphate pentahydrate | 6.0 g |
| | KCl | 5.0 g |
| | Deionized water | 100 ml |
| B | Glycylglycine | 5.0 g |
| | Deionized water | 100 ml |
| C | Biotin (vitamin H) | 2.5 mg |
| | Vitamin $B_{12}$ | 1.5 mg |
| | Deionized water | 100 ml |
| D | $NH_4NO_3$ | 0.5 g |
| | Sodium acetate | 2.5 g |
| | $CaCl_2.2H_2O$ | 0.37 g |
| | Yeast extract | 1.0 g |
| | Peptone | 0.2 g |
| | Deionized water | 500 ml |
| E | $Na_2EDTA$ | 0.75 g |
| | $FeCl_3.6H_2O$ | 97 mg |
| | $MnCl_2.4H_2O$ | 41 mg |
| | $ZnCl_2$ | 5 mg |
| | $CoCl_2.6H_2O$ | 2 mg |
| | $Na_2MoO_4.2H_2O$ | 4 mg |
| | Deionized water | 1000 ml |

Then, this culture solution was concentrated by centrifugation to obtain an algal cell slurry containing 38 g of cells of *Chlamydomonas reinhardtii* UTEX2247 in a volume of 300 ml. This slurry was transferred to a 500-ml Erlenmeyer flask. After nitrogen gas was injected into the slurry for a short period of time to expel oxygen from the flask, it was tightly covered and shaken (at a rate of 65 strokes per minute) under dark conditions to form ethanol. During this period, the pH of the slurry was kept in the range of 6.5 to 8.0 by the addition of 0.1N NaOH or 0.1N HCl.

On the other hand, another algal cell slurry was prepared separately and maintained under the same conditions to form ethanol. In this case, however, no pH regulation was made during the period in which the slurry was shaken in a dark and anaerobic atmosphere.

Figure 3:
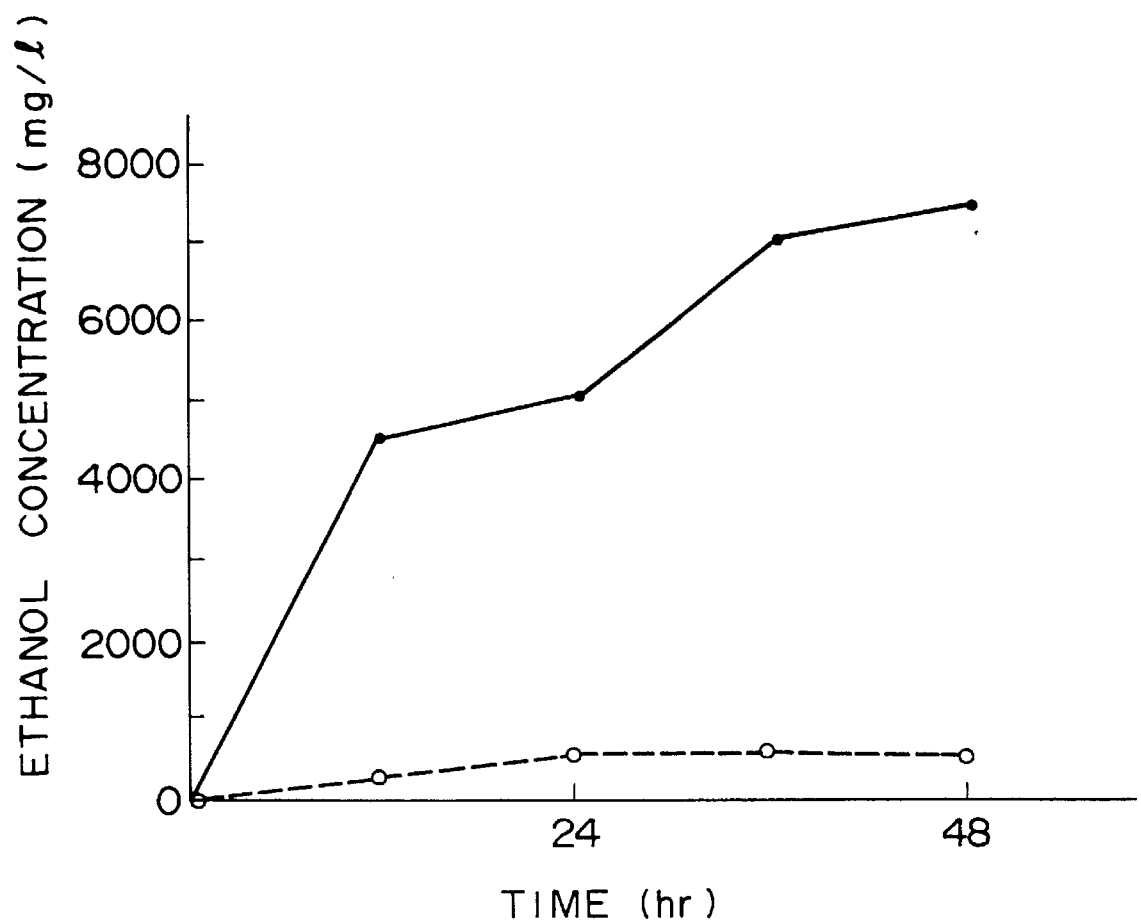
FIG. 3 is a graph showing changes with time of the ethanol concentration of the slurry in Example 2.
Figure 4:
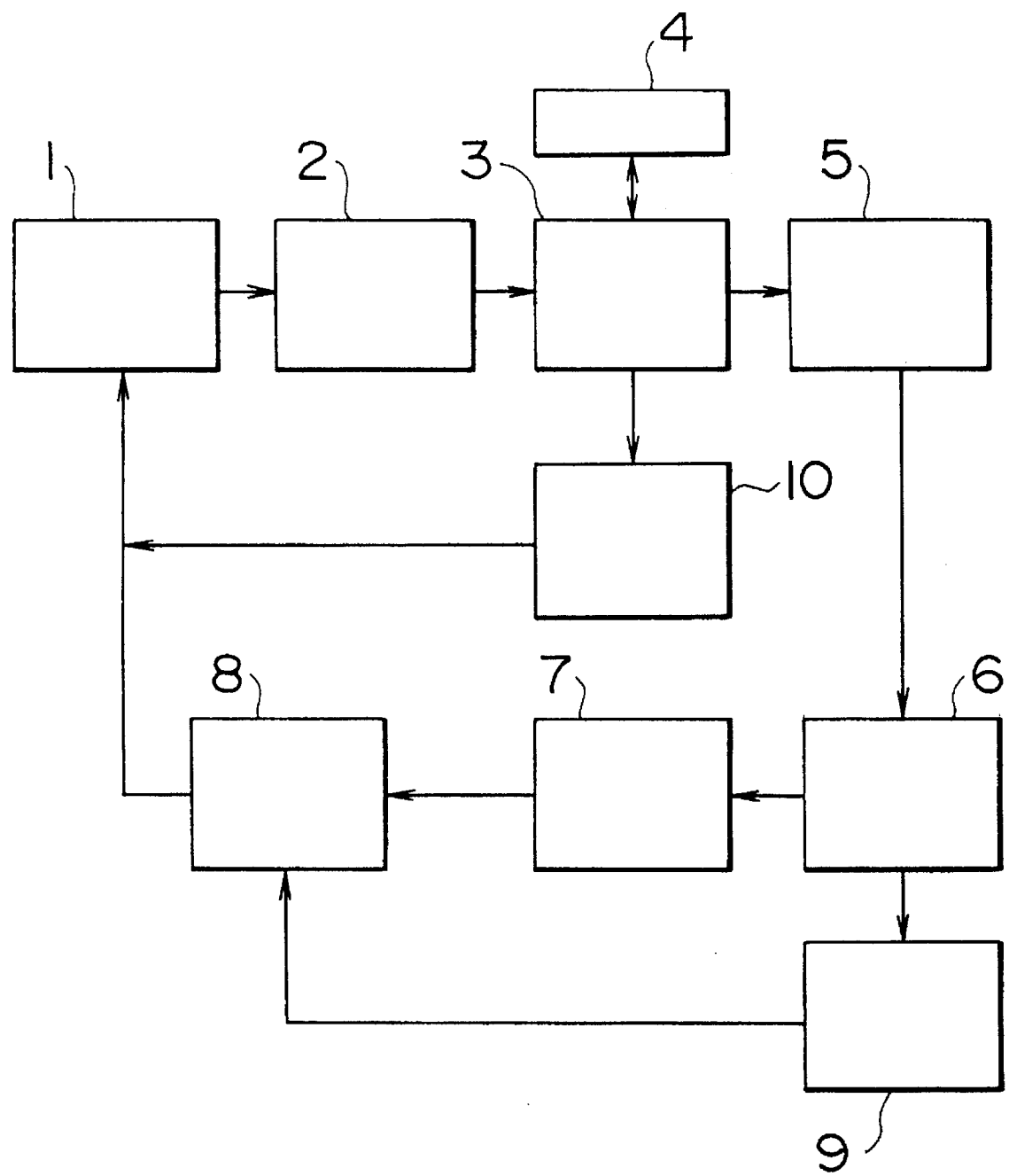
FIG. 4 is a flow diagram schematically illustrating another embodiment of the process for the production of ethanol from microalgae in accordance with the present invention.

Changes with time of the ethanol concentration of the slurry in these two ethanol formation steps are shown in FIG. 3. In FIG. 3, the solid line represents the results obtained when the pH of the slurry was regulated so as to remain in the range of 6.5 to 8.0, and the broken line represents the results obtained when no pH regulation was made. It can be seen from this figure that, when no pH regulation was made, the ethanol concentration remained at a level of as low as 600 mg per liter. The reason for this is believed to be that organic acids (principally lactic acid in the case of *Chlamydomonas reinhardtii* UTEX2247 used in this example) are formed in the slurry from the initial stage of the reaction to reduce its pH to 5.5 and thereby slow down the rate of subsequent ethanol formation.

In contrast, when the pH regulation was made, the ethanol concentration reached a level of as high as 7,500 mg per liter. This indicates that the production of ethanol can be significantly promoted by pH regulation.

The above-described injection of nitrogen gas was carried out in order to establish an anaerobic condition quickly. In practice, because of the respiration (or oxygen consumption) of the concentrated microalgal cells, an anaerobic condition can be established in a relatively short period of time (usually within 30 minutes) without resorting to such means as nitrogen gas injection.

The process in accordance with the second aspect of the present invention is more specifically explained with reference to the following example.

Example 3

*Chlamydomonas reinhardtii* UTEX2247 was cultured in a culture solution composed of culture media A to E having the respective compositions shown in Table 1. More specifically, this culture solution was prepared by mixing 1 ml of A, 10 ml of B, 10 ll of C, 100 ml of D and 6 ml of E, adding water to make a total volume of 1 liter, and adjusting the solution to pH 8.0 with NaOH.

Fifty liters of this culture solution and a stock culture of the above-described *Chlamydomonas* strain (in an amount equivalent to 3.0 g of dried algal cells) were placed in a flat, transparent vessel and cultured at 25° C. for 4 days under continuous illumination at about 15,000 lux with a white fluorescent lamp and with the passage of air (having 5% $CO_2$ added thereto). Thus, there was obtained a culture solution containing 45 g (dry weight) of algal cells in the volume of 50 liters.

Then, this culture solution was concentrated by centrifugation to obtain an algal cell slurry containing 45 g of cells of *Chlamydomonas reinhardtii* UTEX2247 in a volume of 300 ml. This slurry was transferred to a 500-ml Erlenmeyer flask. After nitrogen gas was injected into the slurry for a short period of time to expel oxygen from the flask, it was tightly covered and shaken (at a rate of 65 strokes per minute) under dark conditions to form ethanol. During this period, the pH of the slurry was kept in the range of 7.0 to 8.0 by the addition of 0.1N NaOH or 0.1N HCl.

As a result, ethanol was formed in the first 48 hours and the ethanol concentration reached a maximum of about 9,000 ppm.

Then, this ethanol-containing slurry was heated to separate ethanol by distillation. After the removal of ethanol, the microalga-containing slurry was added to methane fermentation sludge which had previously been acclimatized with microalgal cell components. Thus, the decomposability of the slurry by methane fermentation and the amount of gas so generated were examined. Specifically, when methane fermentation was effected at 35° C. under gently agitated conditions, 60% of the introduced organic matter was decomposed in 10 days and 70% in 15 to 20 days. The amount of gas generated was about 0.45N liter per gram of the introduced organic matter, and this gas was a mixture composed of about 60% of methane and about 40% of carbon dioxide.

Since the lower calorific value of methane is about 8,100 $kcal/Nm^3$, the above gaseous mixture has a calorific value of about 5,000 $kcal/Nm^3$. Thus, it has been found that there is obtained a fuel gas which can be used in boilers and internal combustion engines.

Then, the residue resulting from the methane fermentation treatment was centrifuged (at 3,000G for 10 minutes) to obtain solid matter in the form of a cake containing more than 70% (on a dry weight basis) of organic matter. This solid matter could be dried by exposure to sunlight.

The above-described methane fermentation caused the amount of organic matter to be reduced by 60 to 70%, and the subsequent centrifugation caused 80 to 90% of the organic matter to be removed as solid matter. Thus, it was found that the amount of organic matter present in the supernatant resulting from the centrifugation was reduced to a level of 1/10 to 1/30 of the amount of organic matter present in the residual slurry prior to methane fermentation.

The amount of carbon dioxide necessary for the cultivation of the microalga was about 66 g for 45 g (dry weight) of algal cells. The amounts of carbon dioxide generated in the above-described process were about 11 g during the formation of ethanol in a dark and anaerobic atmosphere, about 21 g during the combustion of the methane fermentation gas, and about 10 g during the combustion of the dried residue resulting from the methane fermentation. Thus, it has been found that 60 to 70% of the carbon dioxide necessary for the cultivation of the microalga can be supplied by recycling the combined amount of carbon dioxide generated to the microalga culturing step.

Figure 1:
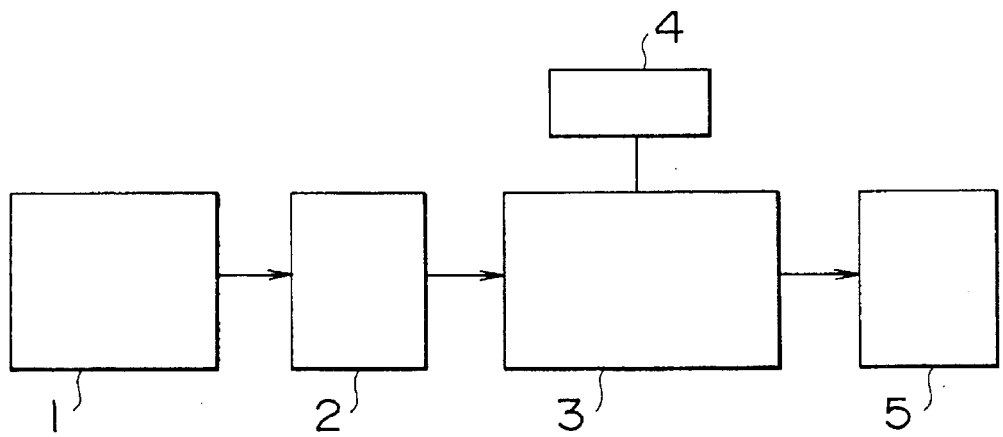
FIG. 1 is a flow diagram illustrating one embodiment of the process for the production of ethanol in accordance with the present invention.

Moreover, a very large amount of energy (such as heat or electricity) is obtained by the combustion of the methane fermentation gas and the dried fermentation residue. Thus, it is possible to recover an amount of energy which is almost equal to all the operating energy of the process of FIG. 1. Accordingly, the process of the present invention produces a triple effect including the recovery of energy in addition to the reduction in the amount of organic waste and the recover and reuse of carbon dioxide.

We claim:

1. A process for the production of ethanol from microalgae which comprises the steps of:

(a) culturing a microalga capable of accumulating starch in the cells thereof in a culture solution;

(b) concentrating the culture solution containing the microalgae cells so as to be as high a solid content as possible, provided that the culture solution contains at least 10% of microalgal cells in dry weight and the flowability of the culture solution is retained;

(c) maintaining the resulting microalgae slurry in a dark and anaerobic atmosphere to form ethanol, while keeping its pH in the range of 6.0 to 9.0;

(d) separating ethanol from the microalgae slurry; and (e) concentrating the separated ethanol.

2. A process for the production of ethanol from microalgae wherein a starch-containing microalga is cultured, harvested, concentrated and then maintained in a dark and anaerobic atmosphere to form ethanol, the process comprising the steps of:

(a) culturing a microalga capable of accumulating starch in the cells thereof in a culture solution;

(b) concentrating the culture solution containing the algal cells to obtain a concentrated microalgae slurry;

(c) maintaining the concentrated microalgae slurry in a dark and anaerobic atmosphere to form ethanol, while keeping its pH in the range of 6.0 to 9.0;

(d) separating the ethanol so formed from the microalgae slurry and concentrating the separated ethanol;

(e) subjecting the microalgae slurry from which ethanol has been separated to methane fermentation in methane fermentation means;

(f) burning the methane-containing fermentation gas generated by the methane fermentation;

(g) drying and burning the residue resulting from the methane fermentation; and (h) recycling the carbon dioxide generated in steps (c), (f) and (g) to the microalga culturing step.

3. The process for the production of ethanol from microalgae according to claim 1 wherein the genus of the microalga is selected from a group consisting of *Chlamydomonas, Chlorella, Spirulina, Oscillatoria* and *Microcystis*.

4. The process for the production of ethanol from microalgae according to claim 2 wherein the genus of the microalga is selected from a group consisting of *Chlamydomonas, Chlorella, Spirulina, Oscillatoria* and *Microcystis*.

* * * * *